United States Patent
Gavronsky

(10) Patent No.: US 6,836,686 B2
(45) Date of Patent: Dec. 28, 2004

(54) ELECTRO-ACUPUNCTURE DEVICE

(76) Inventor: Stas Gavronsky, 39 Wayland Hills Rd., Wayland, MA (US) 01778

(*) Notice: Subject to any disclaimer, the term of this patent is extended or adjusted under 35 U.S.C. 154(b) by 542 days.

(21) Appl. No.: 10/068,826

(22) Filed: Feb. 11, 2002

(65) Prior Publication Data
US 2003/0153963 A1 Aug. 14, 2003

(51) Int. Cl.$^7$ .............................................. A61B 17/34
(52) U.S. Cl. ........................... 607/46; 607/115; 128/907
(58) Field of Search .......................... 607/46, 115, 142, 607/144–145, 148; 128/907

(56) References Cited

U.S. PATENT DOCUMENTS

| | | | | |
|---|---|---|---|---|
| 3,957,053 A | * | 5/1976 | Woo | 606/189 |
| 5,540,710 A | * | 7/1996 | Yoo | 606/189 |
| 5,857,968 A | * | 1/1999 | Benja-Athon | 600/372 |
| 5,961,453 A | * | 10/1999 | Benja-Athon | 600/372 |
| 6,122,547 A | | 9/2000 | Benja-Athon | 607/46 |

* cited by examiner

Primary Examiner—Carl Layno

(57) ABSTRACT

A device according to the invention is comprised of a specially designed electrode and a lead wire for use in electroacupuncture procedure to supply electric pulses to the patient's skin via acupuncture needles. The device is intended for use with a standard electric pulse generator for electro-acupuncture procedure. The electrode consists of a fin made of a thin metal plate or foil that possesses electro-conductive properties, has a substantially rectangular or triangular shape and possesses rigidity in the direction of the acupuncture needle. The corners of the rectangular to triangular electrode can be rounded in order to prevent scratching of the patient's skin. The plate-like electrode has a hole on one edge for connection of a lead wire from the electric pulse generator and a thickened portion on the other edge with a blind hole for insertion of the acupuncture needle. On the side opposite to the insertion of the acupuncture needle, this hole can be closed by a cap to prevent sliding of the electrode towards the patient's skin. This cap also can be conveniently used for pushing on the needle for additional manual needle stimulation. The electric connection formed by a lead wire and electrode made of a thin plate or foil makes it possible to significantly reduce the weight of the device and thus to prevent deformation that might be caused by heavy alligator clamps used in accordance with a conventional practice.

19 Claims, 5 Drawing Sheets

ELECTRO-ACUPUNCTURE DEVICE

FIELD OF THE INVENTION

The present invention relates to the field of non-traditional medicine, in particular to acupuncture, and more specifically, to an electro-acupuncture device.

BACKGROUND OF THE INVENTION

Acupuncture is a form of traditional Chinese medicine that encourages the body to heal itself naturally. It is over 5,000 years old and considered one of the most beneficial ways of restoring balance to the body. Traditional Chinese medicine doctors believe that acupuncture revitalizes our qi, the energy force that flows through the body in pathways known as meridians. Through the painless insertion of very fine needles into specific acupuncture points along the meridians, acupuncture unblocks qi and makes us less susceptible to disease, infection and stress.

Western medicine explains acupuncture's success differently. Some scientists link qi to endorphins—natural pain-killing chemicals—that are released in the needling process, while other scientists believe that acupuncture stimulates muscle tissue, which then alters the nervous system and allows the body to self-heal internal organs. Recent research has also found that acupuncture relieves pain because it changes the brain's chemistry.

Today, there are several alternative forms of acupuncture being performed; the most popular ones are ear acupuncture, or auriculotherapy, acupressure, electrostimulation and moxibustion. Ear acupuncture is highly popular because the ear alone has 200 acupuncture points. Acupressure is the use of hands or a small, flat instrument to stimulate the acupuncture points.

Electrostimulation is the use of local electricity to stimulate acupuncture points, and moxibustion is the use of special herb to stimulate acupuncture points thermally. Depending on specific condition, an acupuncturist chooses the best treatment for the patient.

Electro-acupuncture refers to the procedure of applying small amounts of electricity to needles or staples applied to the skin at acupuncture points. In 1958 when the Chinese were developing methods of acupuncture for surgical anaesthesia, which necessitated long periods of manual manipulation, it was found to be more effective to stimulate the needles electrically by attaching flexible wires, via small crocodile clips, to the needles from a pulse generator. Electroacupuncture was reborn and later introduced into clinical practice on a more general basis for the treatment of pain and neurological disorders. Usually 4–8 needles can be stimulated at one time via parallel channels on the stimulator. One pair of needles inserted into two acupuncture points, wires and a pulse generator outlet is required to complete one circuit. Pulses of electricity are applied to the needles in order to stimulate nerves via the acupuncture point.

U.S. Pat. No. 6,122,547 issued in 2000 to Benja-Athon describes a consolidated electrical-lead acupuncture needle for electroacupuncture and is aimed at prevention of transmission of infectious organisms such as bacteria, virus, and fungus between patients and acupuncturists in electroacupuncture. It is stated in the aforementioned patent that transmission of infections and diseases in electroacupuncture between patients and acupuncturists is well documented in the scientific literature (Ernst E. et al. Life-threatening adverse reactions after acupuncture? A systematic review. Pain 71: 123–126, 1997). Two of the reasons are that there is a lack of sterile equipment and technique and the disregards for using sterile equipment and technique. The design deficiency of the prior art of acupuncture pin and equipment significantly contributed to aforementioned problems.

Presently, electroacupuncture uses the micron-thick shaft of a metallic needle grasped by a relatively larger alligator clip. Alligator clip is attached to one end of an electrical lead, which, in its turn, is attached to the electrical machine. The electrical lead of prior art consists of a plastic-insulated wire with one end connected to a grasping device such as a crocodile clip and the opposite end connected to the electrical stimulator. To establish the flow of electrical current from the electrical lead to the shaft of the acupuncture needle, the crocodile clip grasps onto the micron-thick shaft of the acupuncture needle for the purpose of transmitting electrical current from the stimulator via the wire, the grasping device, and the acupuncture needle, into the patient.

Among other things, it is stated in the aforementioned patent that the connection between crocodile clip and the micron-thick shaft of the acupuncture needle is loose and poor. The crocodile clip is not designed for the purpose of grasping the micron-thin shaft of the acupuncture needle whose diameter is too small to be effectively grasped by the crocodile clip. As a result, unreliable delivery of correct ampere and voltage of the electrical current to the acupuncture needle is common. Second, the contact parts of the crocodile clip, after so many uses, are often oxidized rendering the clip ineffective due to a barrier of a layer of nonconductive oxidized matters.

Breaching of the sterile technique is common. First, the crocodile clip and the electrical lead, which are not sterile to start, will not fix to one position site of the shaft of the acupuncture needle and will slide toward the acupuncture site of the skin during the application of the electrical lead leading to the contamination of the acupuncture skin site and, consequently, the transmission of infectious organisms via the acupuncture site of the skin. Second, the electrical lead and the crocodile clip are reused from patient to patient. Even though the acupuncture needle is sterile, the crocodile clip and its electrical lead are not sterile.

Heavy crocodile clip tends to swing loosely in the air without a means of attaching to the skin, consequently, causing the weight of the electrical lead to easily dislodge the percutaneously implanted acupuncture needle and exposing the sharp tip of the acupuncture needle to inadvertently puncture the fingers of the acupuncturists resulting in the transmission of diseases in electroacupuncture.

The acupuncture needle and, therefore, the sharp tip of the shaft are difficult to visualize, especially in the clinical settings and, consequently, inadvertent puncture of the fingers of the acupuncturists is common leading to the transmission of diseases in electroacupuncture.

It is offered, in the aforementioned patent, to solve the problems described in connection with the conventional electro-acupuncture needles and connections of the needles to the conductive wires by utilizing an integrated electrical-lead acupuncture needle comprising 1) a first electrical lead member as the first physical continuation of a second electricity-conducting shaft member wherefore adaptable to variably adjust and change the length of said shaft member, 2) a rigid or semi-rigid plastic cannular handle member comprises a bore and a first bevelled opening at the first bevelled end for the passage of said shaft member and incrementally and successively the entire said shaft member, and a second square opening at the end of said bore for the passage of said shaft member and said electrical lead. One portion of said shaft member is housed and fits in the bore and the other portion of said shaft member is beyond said bevelled opening of the cannular handle member. The length of the [first] shaft member within said bore is dictated by the length of said handle member but the [second] shaft member beyond said bevelled opening can be variably changed and adjusted by incrementally extending from and retracting into said bore by pushing and pulling, respectively, said electrical lead so that in the latter setting the entire length including the tapered sharp tip of said shaft member can be housed in and sheathed within said bore of said handle member. The electrical lead comprises a first enlarged and fixed spiral stopper portion to encumber the electrical lead beyond the bore of the handle. The second shaft member comprises a second enlarged and fixed spiral stopper portion to encumber second electricity-conducting shaft member beyond the bore of the handle. The third stopper is the second square opening of the handle member. The device includes adhesive on the handle for reversibly affixing the unit to the skin of human. Aforementioned features compel the acupuncturist to discard said unit after one single use on a patient.

Unfortunately, while addressing safety issues, the aforementioned patent offers little help to solve problems related to the weight and, hence, to the mechanical torque which the electrical lead member and the connection means apply to the needle. This torque makes the inserted portion of the needle shift inside the punctured tissues. It causes pain, discomfort, and can sometimes pull the shallowly inserted needle out completely. Furthermore, the usage of the device of the aforementioned patent is limited to "either monopolar pin, monopolar needle, concentric needle electrode or concentric pin electrode". Typical modern acupuncture needle has a shaft and a bigger handle.

OBJECTS AND SUMMARY OF THE INVENTION

It is an object of the present invention to provide an electroacupuncture device which is simple in construction, convenient in use, simplifies the electroacupuncture procedure, prevents transmission of infectious organisms such as bacteria, virus, and fungus between patients and acupuncturists in electroacupuncture, does not use heavy alligator clips for electrical contact between the electrical pulse generator and the needle, improves reliability of the aforementioned electrical contact, prevents oxidation of the contact parts, and makes it possible to significantly reduce the weight of current transfer parts connected to the needle.

The device according to the invention comprises specially designed electrodes and lead wires for use in electroacupuncture procedure that supply electric pulses to the patient's skin via acupuncture needles. The device is intended for use with a standard electric pulse generator for electro-acupuncture procedure. The electrode consists of a fin made of a thin metal plate or foil that possesses electroconductive properties, has a substantially rectangular or triangular shape, and possesses rigidity in the direction of the acupuncture needle. The corners of the rectangular or triangular electrode can be rounded in order to prevent scratching of the patient's skin. The plate-like electrode has a hole on one edge for connection of a lead wire from the electric pulse generator and a thickened portion on the other edge with a blind hole for fitting the electrode onto the handle of the acupuncture needle. On the side opposite to the insertion of the acupuncture needle, this hole can be closed by a cap that can be conveniently used for pushing on the needle for inserting the needle tip into the patient's skin. In order to protect the wire-contact hole from rupture by the lead wire, the wire-contact hole can be reinforced. The depth of the opening for a needle is equal or slightly grater than the length of the handle of the needle in order to prevent physical contact between the lower edge of the fin and the skin of the patients when the electrode is placed on the pre-inserted needle. The fin should have dimensions convenient for grasping with the practitioner's fingers. The lead wire is very thin and light, and preferably is made of copper. One end of the lead wire is exposed and has a hook-like shape for insertion into and engagement with the reinforced hole in the edge of the fin, while on the opposite end the wire may have a standard adaptor for connection to the electric pulse generator. According to another embodiment, the electrode is formed by wrapping a piece of metal foil, having a preformed hole for connection to the lead wire, around the needle handle leaving the tip of the needle projecting outside from the wrapped portion and leaving the hole exposed in an unwrapped portion.

DETAILED DESCRIPTION OF THE INVENTION

Figure 1:
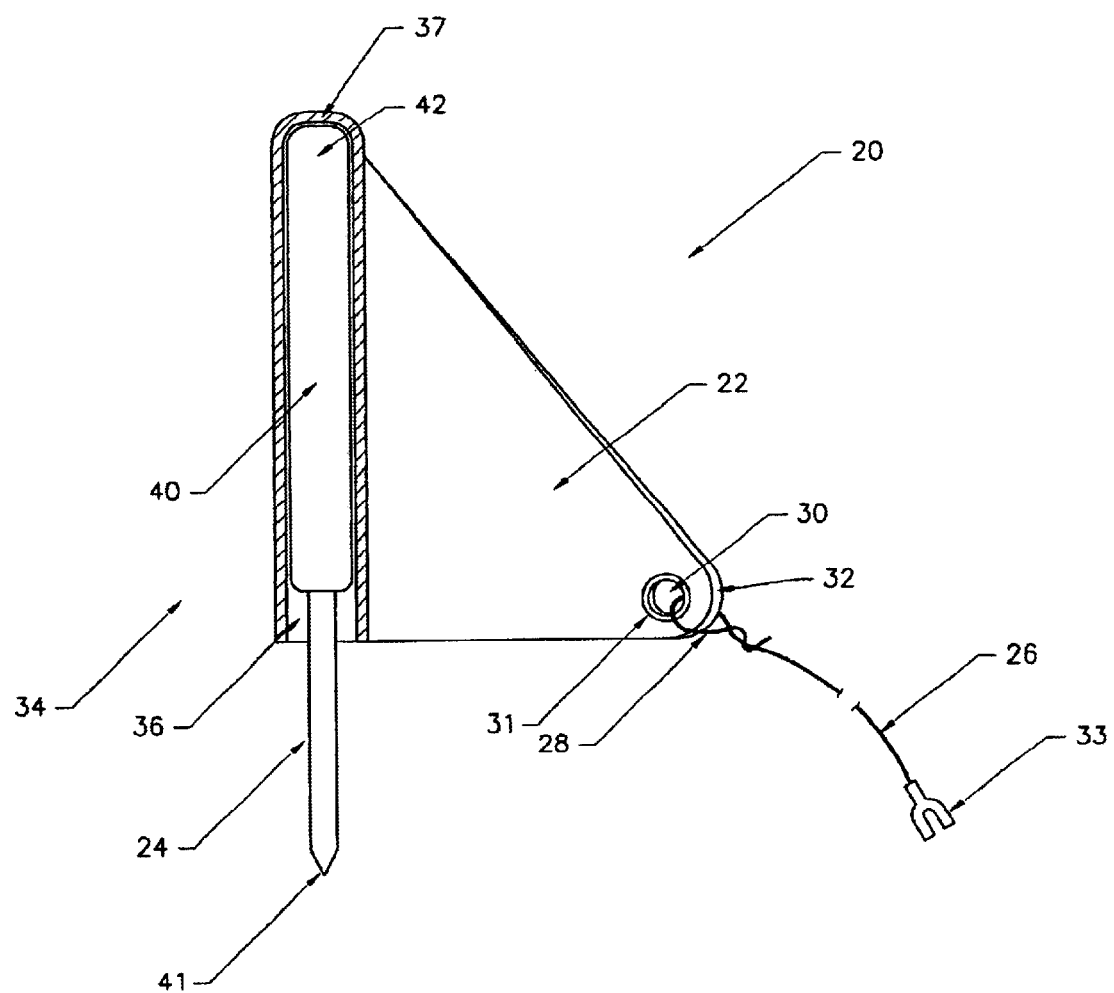
FIG. 1 is a side view of an acupuncture device of the invention with a substantially triangular fin portion and reinforced edge.

Various embodiments of the of the invention are shown in FIGS. 1–4. FIG. 1 is a side view of an acupuncture device of the invention with a substantially triangular fin portion. The device, which in general is designated by reference numeral 20, comprises specially designed flat thin-walled electrode 22 of a substantially triangular shape made from a thin metal plate or a foil having electroconductive properties for transfer of electric pulses to the patient's skin via acupuncture needle 24 from a standard electric pulse generator for electro-acupuncture procedure (not shown) via a lead wire 26. One end 28 of the lead wire 26 is exposed and has a hook-like shape for insertion into a hole 30 punched in the fin 22 for electrical contact with the electroconductive material of the fin 22. The other end 33 of the lead wire 26 is suitable for connection to a terminal of an electric pulse generator (not shown) used for electro-acupuncture.

In order to impart to the fin 22 rigidity in the plane of the fin, the upper edge 32 of the fin 22 can be reinforced, e.g., by making it with an increased thickness, as compared to the thickness of the plate or foil from which the fin 22 is formed. The corners of the triangular electrode can be rounded in order to prevent scratching of the patient's skin. The hole 30 into which the lead wire 26 is inserted is located near one side edge 32 of the electrode. In order to protect the hole 30 from rupture by the lead wire 26, the edge 31 of the hole 30 can be reinforced.

The side edge 34 opposite to edge 32 is made thicker than the thickness of the plate or foil and has a blind hole 36 along the entire edge 34 for insertion of an acupuncture needle 24. The hole 36 terminates in a cap 37 that can be used for pushing on the needle for insertion into the patient's skin. The cap 37 may have a rounded shape. The depth of the hole 36 is shorter than the length of the needle 24 to the extent that after insertion of the needle tip 41 into the patient's skin the electrode does not have physical contact with the skin. The fin 22 should have dimensions convenient for grasping with the practitioner's fingers.

The lead wire 26 is very thin and light and is made preferably of copper. One end of the lead wire 26 is exposed and has a hook-like shape for insertion into and engagement with the reinforced hole 30, while on the opposite end (not shown) the wire may have a standard adaptor for connection to the electric pulse generator. If necessary, after insertion into the hole 30, the hook-like end of the wire can be crimped.

Figure 2:
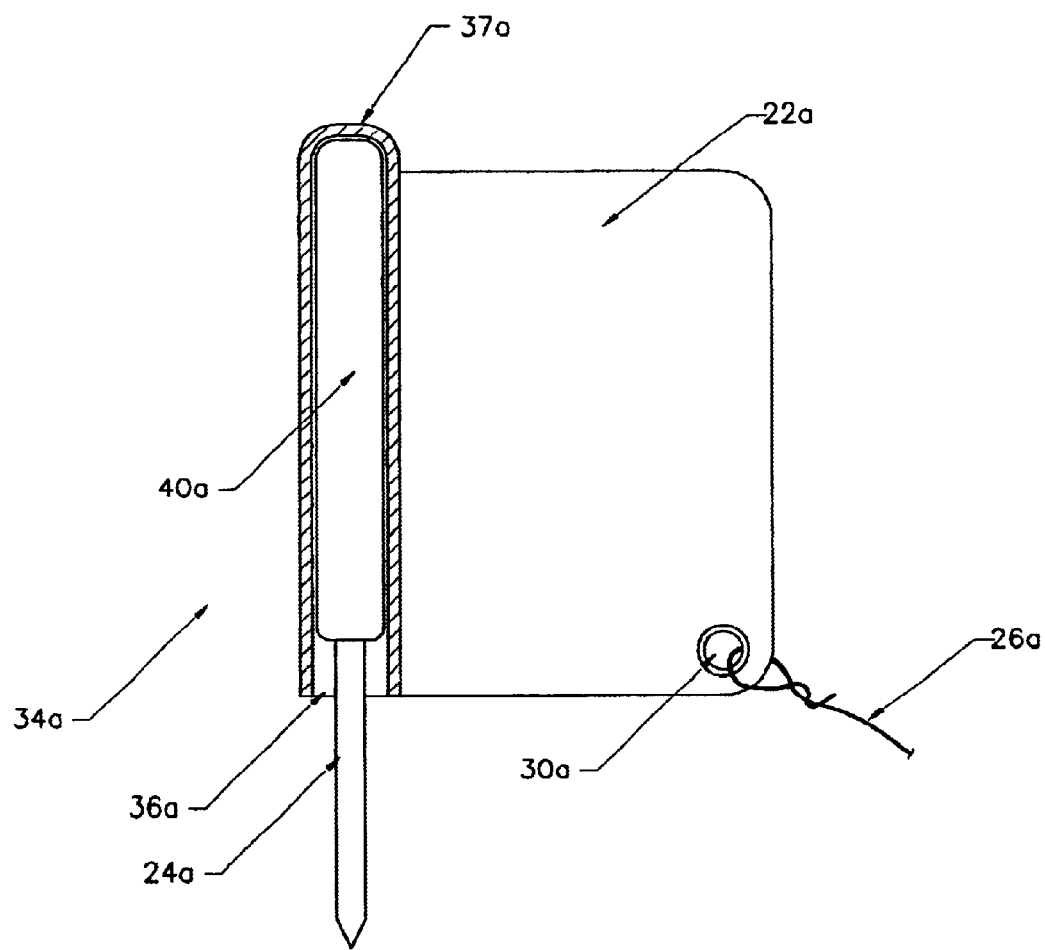
FIG. 2 is a side view of an acupuncture device of the invention with a substantially rectangular fin portion.

FIG. 2 is a side view of an acupuncture device made in accordance with another embodiment, which differs from the embodiment of FIG. 1 only by a rectangular shape of the flat electrode 22a. The remaining parts, such as a thickened portion 34a with a hole 36a for an acupuncture needle 24a and a cap 37a for pushing on the needle, as well as a reinforced opening 30a for a lead wire 26a are identical to similar parts of the previous embodiment.

Figure 3:
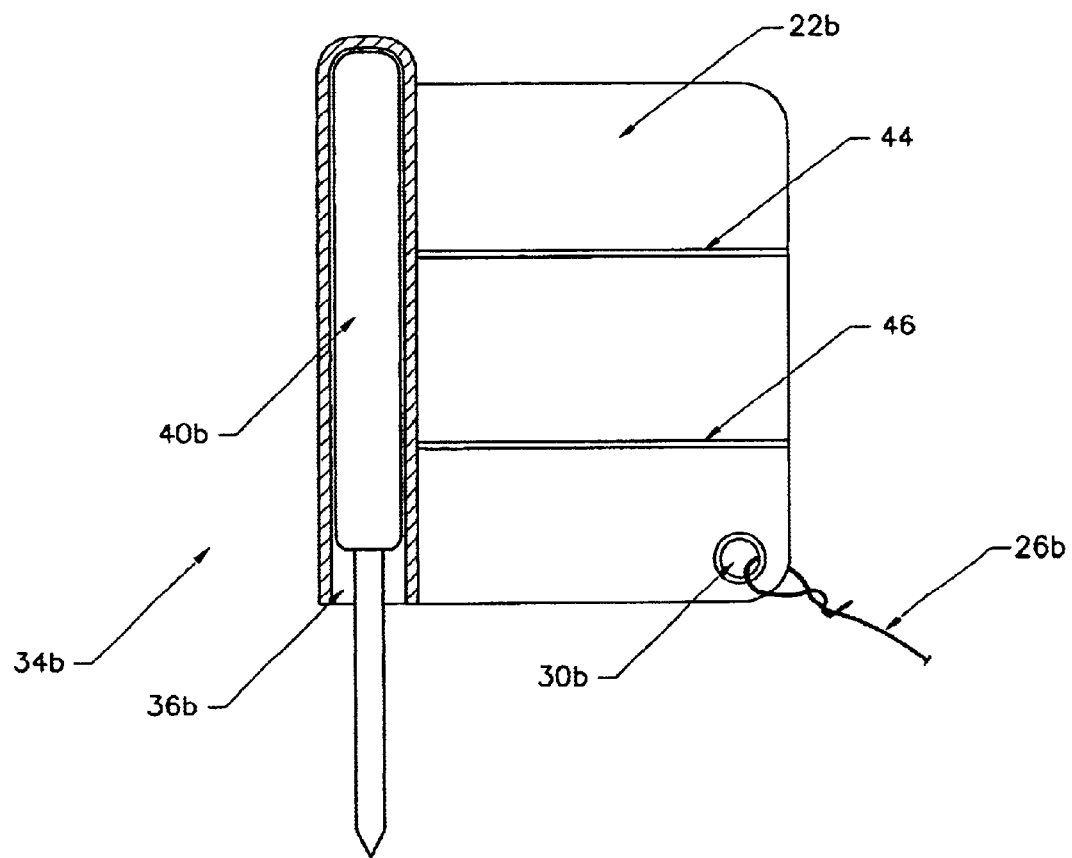
FIG. 3 is a side view of an acupuncture device of the invention with rigidity ribs in the fin portion.

FIG. 3 is a side view of an embodiment of the invention, which is practically the same as the one shown in FIG. 2 with the only difference that the flat electrode 22b is provided with rigidity ribs 44 and 46 formed in the plane of the flat electrode 22b. These ribs impart rigidity to the thin-walled flat electrode and protect it from bending under the weight of the lead wire 26b attached thereto through the opening 30b.

Figure 4:
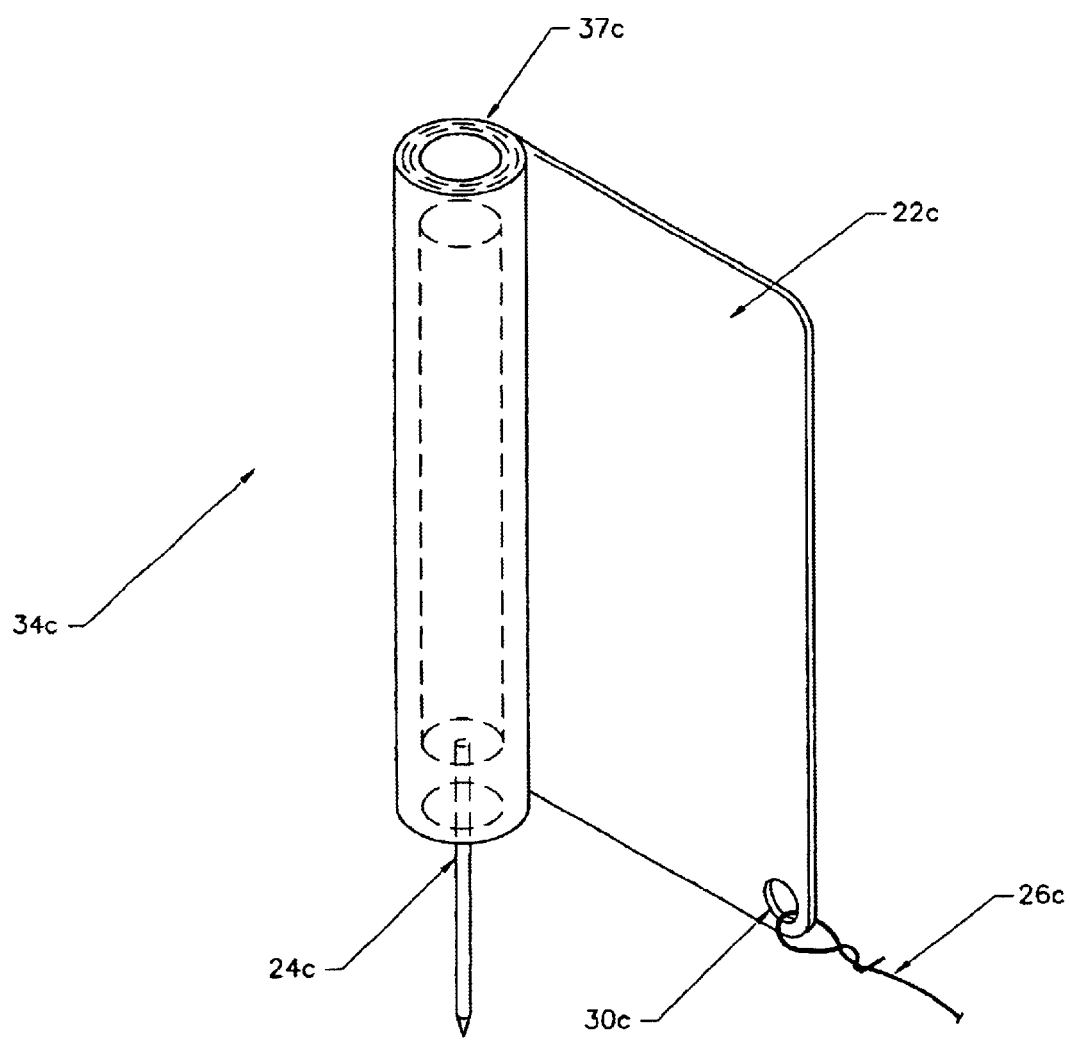
FIG. 4 is a three-dimensional view of an acupuncture device of the invention formed by wrapping a foil around the needle handle.

FIG. 4 is a three-dimensional view of an acupuncture device of the invention formed by wrapping a foil 22c around the needle handle 40c. This is a simplified version of the device that can be prepared by the practitioner prior to the use. In this case, the electroacupuncture kit obtained by the practitioner from the supplier of the acupuncture equipment will contain needles 24c, lead wires 26c, and flat electrodes 22c with preformed holes 30c on one edge of each flat electrode. It is understood that the first turn of wrapping is started from the edge of the electrode opposite to the hole 30c. In order to form a pushing portion 37c that may be used as the cap of the previous embodiments, the upper edge of the wrapping foil should be raised above the upper end of the needle handle 40c. It is also understood that the electrode 22c of this embodiment should not have rigidity ribs of the type shown in FIG. 3.

Figure 5:
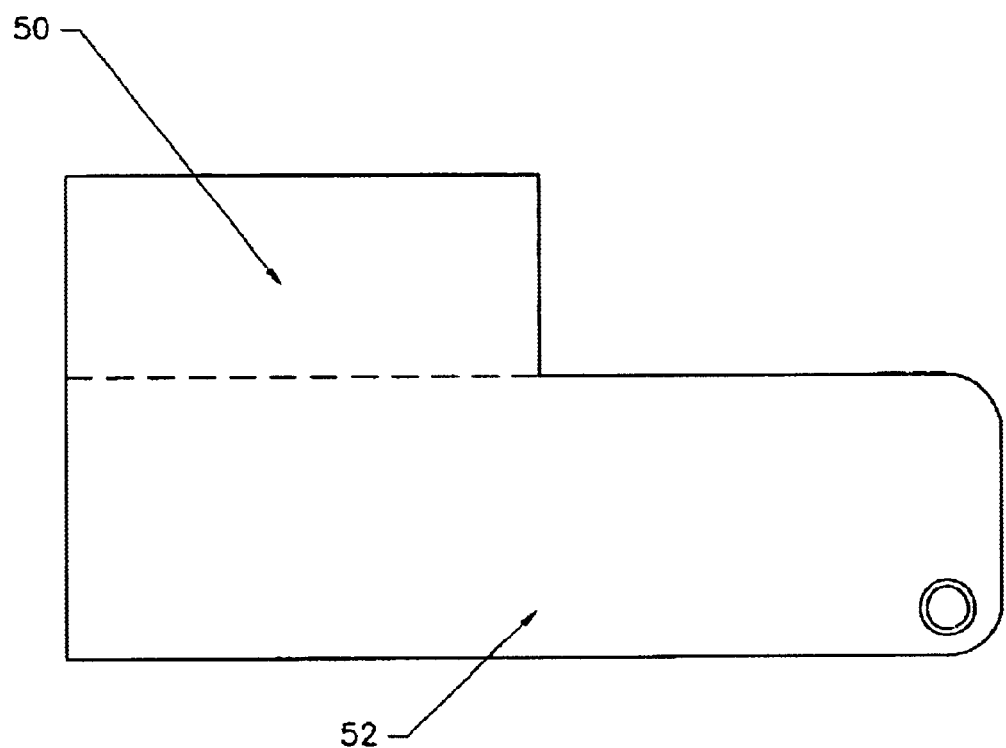
FIG. 5 is a view on a smaller scale illustrating an alternative pattern of the electrode for the embodiment of FIG. 4.

FIG. 5 is a view on a smaller scale illustrating an alternative pattern of the electrode for the embodiment of FIG. 4. In this pattern, a portion 50 is slightly higher than the portion 52 in order to facilitate portion of the cap portion 37c.

The devices of the embodiments shown in FIGS. 1–3 can be supplied in a pre-assembled state with needles and lead wires inserted into the hole 36 till contact with the bottom of the hole in the cap 37. In this case, if the device is disposable, the exposed ends of the lead wires can be soldered to the conductive edges of the hole and the point of connection can be isolated.

In use, the practitioner may fit the electrode 22, 22a, or 22b onto the needle handle 40 by placing it on top of the pre-inserted needle through the hole 36, 36a, or 36b till positions shown in FIGS. 1–3. The practitioner is then connects the lead wire 26, 26a, or 26b to the electric pulse generator (not shown) and performs the electro-acupuncture procedure, as required.

In the case of the embodiment shown in FIGS. 4 and 5, a practitioner wraps the thin-walled electrode around the needle to form a tubular portion 34c and a cap 37c.

Thus it has been shown that the electroacupuncture device of the invention is simple in construction, convenient in use, simplifies the electroacupuncture procedure, prevents transmission of infectious organisms such as bacteria, virus, and fungus between patients and acupuncturists in electroacupuncture, does not use heavy crocodile clips for electrical contact between the electrical pulse generator and the needle, improves reliability of the aforementioned electrical contact, prevents oxidation of the contact parts, and makes it possible to significantly reduce the weight of current transfer parts connected to the needle.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, rigidity ribs may be arranged in any direction, provided they are in the plane of the flat electrode and are not parallel to the needle. The electrode may have a shape different from triangular and square, e.g., a semi-circular shape. The opening for the lead wire may have an oval or a rectangular shape, or two small openings can be provided for threading the wire end through both of them for reliability of the electrical connection. The electrode may be formed without the cap with a through opening for an acupuncture needle, so that the practitioner could squeeze the electrode between the thumb and the middle finger and to push on the projecting needle handle with the pointing finger.

What is claimed is:

1. An electroacupuncture device comprising:

an acupuncture needle having a length, a handle, and a tip;

a flat thin-walled electrode which is made from an electroconductive material and has at least one opening passing through said flat thin-walled electrode in the direction perpendicular to the plane of said flat thin-walled electrode and at least one thickened portion in the plane of said flat thin-walled electrode with a blind opening having a depth, longitudinal axis substantially in the plane of said flat thin-walled electrode and having a diameter sufficient to fit onto said handle, said depth of said blind opening being equal or slightly greater than the length of said handle; and a lead wire electrically connected to said electrode.

2. The electroacupuncture device of claim 1, wherein said flat thin-walled electrode has a shape selected from a group consisting of a substantially triangular shape and a substantially rectangular shape.

3. The electroacupuncture device of claim 2, wherein said flat thin-walled electrode has at least one rigidity rib formed in said plane of said flat thin-walled electrode in any direction, except for the direction parallel to said acupuncture needle.

4. The electroacupuncture device of claim 3, wherein said rigidity rib is formed along an edge of said flat thin-walled electrode.

5. The electroacupuncture device of claim 1, wherein said at least one opening passing through said flat thin-walled electrode in the direction perpendicular to the plane of said flat thin-walled electrode is reinforced.

6. The electroacupuncture device of claim 5, wherein said flat thin-walled electrode has a shape selected from a group consisting of a substantially triangular shape and a substantially rectangular shape.

7. The electroacupuncture device of claim 6, wherein said flat thin-walled electrode has at least one rigidity rib formed in said plane of said flat thin-walled electrode in any direction, except for the direction parallel to said acupuncture needle.

8. The electroacupuncture device of claim 7, wherein said rigidity rib is formed along an edge of said flat thin-walled electrode.

9. The electroacupuncture device of claim 1, wherein on the side opposite to said tip of said needle said thickened portion has a cap that projects above said flat thin-walled electrode and is intended for pushing on said acupuncture needle.

10. The electroacupuncture device of claim 9, wherein said flat thin-walled electrode has a shape selected from a group consisting of a substantially triangular shape and a substantially rectangular shape.

11. The electroacupuncture device of claim 10, wherein said flat thin-walled electrode has at least one rigidity rib formed in said plane of said flat thin-walled electrode in any direction, except for the direction parallel to said acupuncture needle.

12. The electroacupuncture device of claim 11, wherein said rigidity rib is formed along an edge of said flat thin-walled electrode.

13. The electroacupuncture device of claim 9, wherein said at least one opening passing through said flat thin-walled electrode in the direction perpendicular to the plane of said flat thin-walled electrode is reinforced.

14. The electroacupuncture device of claim 13, wherein said flat thin-walled electrode has a shape selected from a group consisting of a substantially triangular shape and a substantially rectangular shape.

15. The electroacupuncture device of claim 14, wherein said flat thin-walled electrode has at least one rigidity rib formed in said plane of said flat thin-walled electrode in any direction, except for the direction parallel to said acupuncture needle.

16. The electroacupuncture device of claim 1, wherein said thickened portion is formed by wrapping said acupuncture needle with said flat thin-walled electrode so that at least one opening passing through said flat thin-walled electrode in the direction perpendicular to the plane of said flat thin-walled electrode remains exposed.

17. The electroacupuncture device of claim 16, wherein said flat thin-walled electrode has an upper edge and wherein said wrapping is carried out in a position in which said edge is located above said handle of said acupuncture needle.

18. The electroacupuncture device of claim 17, wherein said flat thin-walled electrode has a shape selected from a group consisting of a substantially triangular shape and a substantially rectangular shape.

19. The electroacupuncture device of claim 18, wherein said at least one opening passing through said flat thin-walled electrode in the direction perpendicular to the plane of said flat thin-walled electrode is reinforced.

* * * * *